(12) United States Patent
Plack

(10) Patent No.: US 12,369,606 B1
(45) Date of Patent: Jul. 29, 2025

(54) METHOD OF DETERMINING THE MASS BALANCE CLOSURE QUANTIFICATION OF FIBER OF A SAMPLE

(71) Applicant: Soliton, LLC, Sioux Falls, SD (US)

(72) Inventor: Kristi Plack, Harrisburg, SD (US)

(73) Assignee: Soliton, LLC, Sioux Falls, SD (US)

( * ) Notice: Subject to any disclaimer, the term of this patent is extended or adjusted under 35 U.S.C. 154(b) by 0 days.

(21) Appl. No.: 18/120,186

(22) Filed: Mar. 10, 2023

Related U.S. Application Data

(63) Continuation of application No. 16/400,766, filed on May 1, 2019, now abandoned, which is a continuation-in-part of application No. 15/886,452, filed on Feb. 1, 2018, now abandoned.

(60) Provisional application No. 62/455,250, filed on Feb. 6, 2017.

(51) Int. Cl.
| | |
|---|---|
| *C08L 91/00* | (2006.01) |
| *A23K 10/38* | (2016.01) |
| *A23L 7/10* | (2016.01) |
| *A23L 7/104* | (2016.01) |
| *B02B 1/02* | (2006.01) |
| *C12P 7/06* | (2006.01) |
| *B02B 5/02* | (2006.01) |

(52) U.S. Cl.
CPC ............. *A23K 10/38* (2016.05); *A23L 7/104* (2016.08); *A23L 7/115* (2016.08); *B02B 1/02* (2013.01); *C12P 7/06* (2013.01); *B02B 5/02* (2013.01)

(58) Field of Classification Search
CPC ......... A23K 10/38; A23L 7/104; A23L 7/115; B02B 1/02; B02B 5/02; C12P 7/06
USPC ........................................................ 426/618
See application file for complete search history.

(56) References Cited

U.S. PATENT DOCUMENTS

| | | | |
|---|---|---|---|
| 4,525,218 | A | 6/1985 | Chen et al. |
| 8,399,224 | B2 | 3/2013 | Konieczny-Janda et al. |
| 8,518,467 | B2 * | 8/2013 | Srinivasan .............. A23K 10/38 |
| | | | 426/482 |
| 8,679,793 | B2 | 3/2014 | Lewis |
| 9,200,302 | B2 | 12/2015 | Comettini et al. |
| 9,335,043 | B2 | 5/2016 | Nguyen |
| 10,138,332 | B2 | 11/2018 | Jansen et al. |
| 2013/0164795 | A1 | 6/2013 | Lowe et al. |
| 2013/0309360 | A1 * | 11/2013 | Lewis ...................... A23L 7/104 |
| | | | 426/64 |
| 2015/0216203 | A1 | 8/2015 | Isaksen et al. |
| 2018/0363017 | A1 | 12/2018 | Tolan et al. |

FOREIGN PATENT DOCUMENTS

| | | |
|---|---|---|
| WO | WO 2013/166469 A2 | 11/2013 |
| WO | WO 2014/202711 A1 | 12/2014 |
| WO | WO 2024/091515 A1 | 5/2024 |

OTHER PUBLICATIONS

Adeogun, et al., "$ZnCl_2$ Enhanced Acid Hydrolysis of Pretreated Corncob for Glucose Production: Kinetics, Thermodynamics and Optimization Analysis", 2018, *Journal of Bioresources and Bioproducts*, 4(3):149-158.
Adney, "Measure of Cellulase Activities", Laboratory Analytical Procedure (LAP), Technical Report NREL/TP-510-42628, Issue Date Aug. 12, 1996, edition date Jan. 2008, National Renewable Energy Laboratory (NREL), Golden, Colorado, operated for the U.S. Department of Energy, 11 pages.
AOAC Official Method 930.15 Loss on Drying (Moisture) For Feeds.
AOAC Official Method 935.29 Moisture in Malt.
AOAC Official Method 942.05 Ash of Animal Feed.
AOAC Official Method 945.16 Oil in Cereal Adjuncts Petroleum Ether Extraction Method.
AOAC Official Method 990.03 Protein (Crude) In Animal Feed.
AOAC Official Method 995.16, "β-Glucan in Barley and Oats: Streamlined Enzymatic Method", First Action 1995, AOAC International, Rockville, Maryland, © 2000, 3 pages.
AOAC Official Method 996.11 Starch (Total) in Cereal Products.
ASTM D1696-95 (Reapproved 2019), "Standard Test Method for Solubility of Cellulose in Sodium Hydroxide", Dec. 2019, ASTM International, West Conshohocken, Pennsylvania, 4 pages.
ASTM E3181-20, "Standard Practice for Determination of the Converted Fraction of Starch and Cellulosic Content From a Fuel Ethanol Production Facility", Mar. 2020, ASTM International, West Conshohocken, Pennsylvania, 10 pages.
Cao, et al., "Acid Hydrolysis of Cellulose in Zinc Chloride Solution", 1995, *Applied Biochemistry and Biotechnology*, 51/52:21-28.
Céspedes et al. "Quantification of digestive utilization of dietary fiber from corn co-products in grown pigs", 2015, Dissertation, Iowa State University, Ames, Iowa, 166 pages. Available online at <chrome-extension://efaidnbmnnnibpcajpcglclefindmkaj/https://core.ac.uk/download/pdf/38937737.pdf> Obtained from the internet on Sep. 2, 2023.
"Conversion of Corn-Kernel Fiber in Conventional Fuel-Ethanol Plants", Project No. 0340-19-03 (short version), Nov. 11, 2018, National Corn to Ethanol Research Center (NCERC), Edwardsville, Illinois, 7 pages.
Dahnum et al., "Comparison of SHF and SSF processes using enzyme and dry yeast for optimization of bioethanol production from empty fruit bunch", 2015, *Energy Procedia*, 68:107-116.

(Continued)

*Primary Examiner* — Brent T O'Hern
(74) *Attorney, Agent, or Firm* — Mueting Raasch Group

(57) ABSTRACT

A method of determining the mass balance closure quantification of fiber of a sample includes using an extraction technique followed by analysis of non-saccharide soluble organics (solubles). In conjunction with traditional analyses of protein, fat, starch, and ash, this method accurately determines fiber by mass closure calculation. On pre and post processed grain materials the calculation is fiber=100−protein−fat−starch−ash−solubles. The accurate determination of fiber determines the converted fraction for the generation of D3 RINS by the Environmental Protection Agency's in situ renewable fuels pathway.

11 Claims, No Drawings

(56) References Cited

OTHER PUBLICATIONS

Federal Register, "Part III: Environmental Protection Agency: 40 CFR 40 Part 80, Regulation of Fuels and Fuel Additives: RFS Pathways II, and Technical Amendments to the RFS Standards and E15 Misfueling Mitigation Requirements; Final Rule", Jul. 18, 2014, vol. 79, No. 138, 42128-42167.

Flodman, et al., "Extraction of Soluble Fiber from Distillers' Grains", Dec. 2011, *Applied Biochemistry and Biotechnology*, 166(4):1070-81.

Gao et al., "Fast Hemicellulose Quantification Via a Simple One-Step Acid Hydrolysis", Jun. 2014, *Biotechnology and Bioengineering*, 111(6):1088-1096.

Gibson, "Fiber Frustration", May 10, 2021, Ethanol Producer Magazine, 3 pages. Available online at <www.ethanolproducer.com/articles/18193/fiber-frustration>. Obtained from the internet on May 18, 2021.

Iberahim et al., "Sodium Hydroxide Pretreatment and Enzymatic Hydrolysis of Oil Palm Mesocarp Fiber", Jun. 2013, *Int'l J Chem Eng and Appl*,4(3):101-105.

Janga et al., "Influence of Acid Concentration, Temperature, and Time on Decrystallization in Two-Stage Concentrated Sulfuric Acid Hydrolysis of Pinewood and Aspenwood: A Statistical Approach", 2012, *BioResources*, 7(1):391-411.

Kanchanalai et al., "Reaction Kinetics of Concentrated-Acid Hydrolysis for Cellulose and Hemicellulose and Effect of Crystallinity", 2016, *BioResources*, 11:1672-1689.

Kaur et al., "Efficient process engineering for extraction of hemicellulose from corn fiber and its characterization", 2020, *Carbohydrate Polymer Technology and Applications*, 1:100011, 7 pages. Available online Oct. 13, 2020.

Kukielski et al., "Maximize Ethanol Production from Corn Starch, Resistant Starch, Cellulose and Xylan", NCERC at Southern Illinois University, Edwardsville, Illinois, 14 pages. No date available. Believed to be available as early as Aug. 5, 2021. Available online at fs.hubspotusercontent00.net/hubfs/8341404/FELC%202021%20Yan%20Zhang%20Corn%20Kernel%20Fiber.pdf>.

Li et al., "In-situ corn fiber conversion improves ethanol yield in corn drymill process", Mar. 2018, *Industrial Crops and Products*, 113:217-224.

Mandels et al., "Enzymatic Hydrolysis of Waste Cellulose", 1974, *Biotechnology and Bioengineering, vol. XVI*, John Wiley & Sons, Inc. pp. 1471-1493.

Marlett, et al., "Comparison of In Vitro and In Vivo Measures of Resistant Starch in Selected Grain Products", 1996, Cereal Chemistry, 73(1):63-68. Available online at cerealsgrains.org/publications/cc/backissues/1996/Documents/73_63.pdf>. Obtained from the internet on Sep. 2, 2023.

Megazyme, "Mushroom and Yeast Beta-Glucan Assay Procedure", 2021, Megazyme, Bray, Ireland, 16 pages.

Memorandum to Air and Radiation Docket EPA-HQ-OAR-2012-0401, "Additional Detail on the Calculation of the Cellulosic Converted Fraction, and Attribution of Batch RINs for D-code Dependent Feedstocks", Jul. 1, 2014, U.S. Environmental Protection Agency (EPA), Washington, DC, 11 pages.

Michel et al., "Determination of Cellulosic Glucan Content in Starch Containing Feedstocks," Laboratory Analytical Procedure (LAP), Technical Report NREL/TP-2800-76724, Issue Date Feb. 2021, National Renewable Energy Laboratory (NREL), Alliance for Sustainable Energy, LLC, Golden, Colorado, operated for the U.S. Department of Energy, 20 pages.

Moxley, Thesis, "Studies of Cellulosic Ethanol Production from Lignocellulose", Jun. 8, 2007, Virginia Polytechnic Institute and State University, Blacksburg, Virginia, 82 pages.

Moxley, et al., "More Accurate Determination of Acid-Labile Carbohydrates in Lignocellulose by Modified Quantitative Saccharification", 2007, *Energy & Fuels*, 21:3684-3688. Available online Oct. 18, 2007.

Searle, "A seemingly innocuous cellulosic biofuel pathway", May 28, 2019, International Council on Clean Transportation, 5 pages. Available online at theicct.org/blog/staff/seemingly-innocuous-cellulosic-biofuel-pathway. Obtained from the internet on Apr. 9, 2021.

Sluiter et al., "Compositional Analysis of Lignocellulosic Feedstocks. 1. Review and Description of Methods", 2010, *J Agric Food Chem* 58(16):9043-9053. Published online Jul. 29, 2010.

Sluiter et al., "Determination of Sugars, Byproducts, and Degradation Products in Liquid Fraction Process Samples", Laboratory Analytical Procedure (LAP), Technical Report NREL/TP-510-42623, Issue Date Dec. 8, 2006, edition date Jan. 2008, National Renewable Energy Laboratory (NREL), Golden, Colorado, operated for the U.S. Department of Energy, 14 pages.

Sluiter et al., "Determination of Structural Carbohydrates and Lignin in Biomass", Laboratory Analytical Procedure (LAP), Technical Report NREL-TP-510-42618, Issue Date Apr. 2008, Revision Date Aug. 3, 2012, National Renewable Energy Laboratory (NREL), Alliance for Sustainable Energy, LLC, Golden, Colorado, operated for the U.S. Department of Energy, 18 pages.

Sluiter et al., "Direct determination of cellulosic glucan content in starch containing samples", Jan. 15, 2021, *Cellulose*, 14 pages. Available online at doi-org/10.1007/s10570-020-03652-2.

Sluiter, et al., "Summative Mass Closure", Laboratory Analytical Procedure (LAP) Review and Integration, Technical Report NREL/TP-510-48087, Issue Date Apr. 2010, Revision Date Jul. 8, 2011, National Renewable Energy Laboratory (NREL), Alliance for Sustainable Energy, LLC, Golden, Colorado, operated for the U.S. Department of Energy, 13 pages.

Topic, "Hemicellulose", 2020, *Science Direct*, 12 pages.

Topic, "Xylanases", 2014, *Science Direct*, 10 pages.

Van Soest et al., "Symposium: Carbohydrate Methodology, Metabolism, and Nutritional Implications in Dairy Cattle: Methods for Dietary Fiber, Neutral Detergent Fiber, and Nonstarch Polysaccharides in Relation to Animal Nutrition", 1991, *J Dairy Sci*, 74:3583-3597.

Wang et al., "Comparative Study of Alkali and Acidic Cellulose Solvent Pretreatment of Corn Stover for Fermentable Sugar Production", 2016, *BioResources*, 11(1):482-491.

Wang, "Experiment No. 4, Cellulose Degradation", Department of Chemical & Biomolecular Engineering course ENCH485, University of Maryland, College Park, Maryland, 6 pages. No publication date available, believed to be available as early as 2009. Obtained from the internet May 5, 2021.

Wu et al., "Effect of $H_2O_2$ Bleaching Treatment on the Properties of Finished Transparent Wood", May 1, 2019, *Polymers* 11:773, 13 pages.

Wyman et al., "*Hydrolysis of Cellulose and Hemicellulose*" in Polysaccharides: Structural Diversity and Functional Versatility 995 (Severial Dumitriu ed., 2004). 167 pages plus cover page. Available online Aug. 13, 2015.

Dunning et al., "The Saccharification of Agricultural Residues" Jan. 1945, Industrial & Engineering Chemistry, 37(1):6 pages.

International Patent Application No. PCT/US2023/035825, filed Oct. 24, 2023; International Search Report / Written Opinion issued Feb. 15, 2024; 12 pages.

International Patent Application No. PCT/US2023/035825, filed Oct. 24, 2023; International Preliminary Report on Patentability, mailed Sep. 25, 2024, 39 pages.

* cited by examiner

METHOD OF DETERMINING THE MASS BALANCE CLOSURE QUANTIFICATION OF FIBER OF A SAMPLE

CROSS-REFERENCE TO RELATED APPLICATIONS

This application is a continuation of U.S. patent application Ser. No. 16/400,766, filed May 1, 2019, which is a continuation-in-part of U.S. patent application Ser. Nos. 15/885,452, 15/886,452, filed Feb. 1, 2018, which claims the benefit of U.S. Provisional Application No. 62/455,250 filed Feb. 6, 2017, the disclosures of which are incorporated by reference herein in their entireties.

SUMMARY

The disclosure and prior art relate to methods for quantification of fiber. In one embodiment, the disclosure relates more particularly to a method for quantification of fiber for determining the converted fraction for the generation of D3 Renewable Identification Numbers (hereinafter "RINS") as required by the Environmental Protection Agency (hereinafter "EPA"). D3 is the designation assigned to those biofuels derived from cellulose. Non-limiting examples of applicability of the method of the disclosure would be in the in situ renewable fuels pathway from a dry mill ethanol plant, and any other process for converting fiber, including processes that convert fiber separate from starch and cellulosic processes and processes related to animal nutrition.

Dried distillers grains (hereinafter "DDG") and dried distillers grains with solubles (hereinafter "DDGS") are types of animal food produced at fuel ethanol production facilities. This includes preprocessed and post-process grain materials and is not specific to any sample in the ethanol production process. Residuals are generally defined herein materials remaining after post-processing, i.e. fermentation, has taken place whereas preprocessed materials are those where fermentation has not occurred. As designated herein, the category of "solubles" comprises soluble saccharides (hereinafter "SS") and non-saccharide soluble organics (hereinafter "NSSO"). It is noted that the Environmental Protection Agency has defined "cellulosic content" being specific to the sum of cellulose, hemicellulose, and lignin in cellulosic feedstock, wherein the soluble saccharides may be included with the starch total.

The accurate determination of fiber is critical to determining the converted fraction, which is the percentage of fiber before fermentation with respect to the percentage of fiber after fermentation, for the generation of D3 RINS by the EPA's in situ renewable fuels pathway. Previous methods of fiber analysis by analytical methods are variable, which interferes with the mass balance closure. In fact, about 18%-20% of the mass of post processed grain residuals is currently unknown when using conventional prior art analysis of proximates (i.e. components of the grain including protein, fat, starch, and ash). This unknown percentage of material includes a fiber component which, hereto before now, remained unidentified. For this reason a need for finding the percentage of fiber within the unknown portion of the composition has persisted.

An embodiment of the disclosure meets the needs presented above by generally comprising a method for quantification of fiber in pre and post processed materials for the purposes of establishing the converted fraction for D3 in situ RINS by determining the percentage of soluble saccharides and non-saccharide soluble organics within the pre and post processed materials. Any remaining percentage will comprise fiber that was otherwise undiscoverable by prior art methods.

Therefore, an embodiment of the disclosure generally comprises assays which provide full mass closure on pre-processed grain materials or post processed grain residuals from a dry mill ethanol facility. The methods of the disclosure for determining soluble saccharides and non-saccharide soluble organics are novel analytical methods that complete the mass closure thereby enabling the quantification of fiber by mass closure calculation. The novel SS and NSSO assays use an extraction technique followed by an analysis of soluble saccharides and other solubles, also referred to herein as non-saccharide soluble organics, (lactic acid, glycerol, and acetic acid) by a high-pressure liquid chromatography (hereinafter "HPLC") method.

Using the novel solubles assays of the disclosure on pre-processed grain materials or post processed grain residuals in conjunction with the traditional proximates analyses of protein, fat, starch, and ash provides a way to arrive at an accurate quantification of fiber via mass closure calculation. The novel solubles assays for Soluble Saccharides ("SS") and Non-Saccharide Soluble Organics ("NSSO") of the disclosure are applied, along with the determination of the conventional proximates (protein, fat, starch, ash), to calculate fiber by subtracting all other known components. The quantification of fiber is accomplished by measuring protein, fat, starch, and ash by conventional methods, measuring Soluble Saccharides and Non-Saccharide Soluble Organics by the method of the disclosure on a dry weight basis, and then subtracting the aggregate total from 100%. On residuals, the calculation is:

Fiber=100−(Protein+Fat+Starch+Ash+Solubles (SS and NSSO))

Utilizing, for example, the California Air Resource Board definition of soluble saccharides, wherein an account of C5 and C6 sugars is made by using un-washed starch, the above calculation may become:

Fiber=100−(Protein+Fat+Starch+Ash+Solubles (NSSO))

In accordance with the disclosure, the analytical quantification of the solubles fraction of post and pre-processed grain enables the complete mass closure. The novel solubles assays in conjunction with the traditional proximates analyses of protein, fat, starch, and ash provides a novel method of accurately determining fiber by mass closure calculation. The complete mass closure enables the fiber content to be calculated in lieu of measuring fiber.

Data has shown the manner of calculating fiber in accordance with the disclosure is more precise than measuring fiber by the conventional neutral detergent fiber assay. The accurate determination of fiber is critical to determining the Converted Fraction for the generation of D3 RINS by the EPA's in situ renewable fuels pathway.

The solubles assays on materials in accordance with the disclosure coupled with the calculation of fiber by mass closure allows for the accurate quantification of fiber, which enables the quantification of in situ D3 RINS from a dry mill ethanol plant. The solubles assays of the disclosure coupled with the calculation of fiber by mass closure may also be applied in the area of animal nutrition.

There has thus been outlined, rather broadly, the more important features of the disclosure in order that the detailed description thereof that follows may be better understood, and in order that the present contribution to the art may be better appreciated. There are additional features of the disclosure that will be described hereinafter, and which will form the subject matter of the claims appended hereto.

The objects of the disclosure, along with the various features of novelty which characterize the disclosure, are pointed out with particularity in the claims annexed to and forming a part of this disclosure.

DETAILED DESCRIPTION OF THE INVENTION

A new method of fiber analysis embodying the principles and concepts of an embodiment of the disclosure will be described.

The method of determining the mass balance closure quantification of fiber of a sample generally comprises method is provided for the quantification of fiber in pre and post processed materials for the purposes of establishing the converted fraction for D3 in situ RINS. Quantification of fiber is accomplished by measuring protein, fat, starch, ash, soluble saccharides and non-saccharide soluble organics on a dry weight basis, and then subtracting the aggregate total from 100%.

The methods for determining solubles, i.e. soluble saccharides and non-saccharide soluble organics are analytical methods that complete the mass closure thereby enabling the quantification of fiber by mass closure calculation. The analytical quantification of the solubles fraction of the preprocessed grain and post-processed grain residuals provided by the present disclosure enables the complete mass closure of pre-processed grain materials and post processed grain residuals. The complete mass closure enables the fiber content to be calculated in lieu of measuring fiber. Previous methods of fiber analysis by analytical methods are variable, which interferes with the mass balance closure. In fact, about 18-20% of the mass of post process grain residual is currently unknown when using conventional proximates analysis.

An embodiment of the disclosure provides assays which enable full mass closure on DDG and DDGS and pre-process grains and post process grain residuals. The assays in accordance with the disclosure were invented in an effort to obtain full mass closure on pre-processed grain materials or post processed grain residuals, the animal food produced at fuel ethanol production facilities. The novel assays for SS and NSSO are applied, along with the conventional assays for proximates (protein, fat, starch, ash), to calculate fiber by subtracting all other known components. Data has shown the manner of calculating fiber in accordance with the disclosure is more precise than measuring fiber by the conventional neutral detergent fiber assay. The assays of the disclosure enable accurate determination of fiber, which is critical to determining the converted fraction for the generation of D3 RINS by the EPA's in situ renewable fuels pathway.

Therefore, the solubles assays on pre and post processed materials in accordance with the disclosure coupled with the calculation of fiber by mass closure allows for the accurate quantification of fiber, which enables the quantification of in situ D3 RINS from a dry mill ethanol plant. According to the disclosure, pre-processed grain materials and post processed grain residuals tested by the conventional proximate analysis tests, and by the SS and NSSO assays. The values of the test results are used to calculate a mass closure on the sample and to calculate fiber. Using the solubles assays on preprocessed materials and post processed residuals in conjunction with the traditional proximates analyses of protein, fat, starch, and ash provides a way to arrive at an accurate quantification of fiber via mass closure calculation. The calculation is:

$$Fiber=100-(Protein+Fat+Starch+Ash+Solubles\ (SS\ and\ NSSO))$$

The novel SS and NSSO assays use an extraction technique followed by an analysis of saccharides and other solubles, also referred to herein as non-saccharide soluble organics (lactic acid, glycerol, and acetic acid) by a high-pressure liquid chromatography (hereinafter "HPLC") method, or other suitable methods.

In one embodiment of the disclosure, a weight of sample (5 g) is added to a centrifuge tube, and a weight of water is added (about 19.95 g). This is then extracted at high temperatures (~95 C) for 2 hours. The sample is then centrifuged. The supernatant is analyzed to get a density of the liquid portion, and the remaining liquid portion is filtered for HPLC analysis. The values of the HPLC analysis for sugars and other solubles are entered into a calculation to determine the dry weight value of the Soluble Saccharides and Non-Saccharide Soluble Organics.

The moisture of stocks used must be checked every time new stock is sourced. Protein, fat, ash, starch and moisture are analyzed by recognized methods, and both SS and NSSO are measured by the novel assay of the disclosure. The dry weight values of SS, NSSO, protein, fat, ash starch and moisture are used to calculate the mass balance closure and the fiber. One recognized method for protein analysis is set forth in Association of Official Analytical Chemists (hereinafter "AOAC") Official Method 990.03 Protein (Crude) In Animal Feed. One recognized method for fat analysis is set forth in AOAC Official Method 945.16 Oil in Cereal Adjuncts Petroleum Ether Extraction Method. A recognized method for ash analysis is set forth in AOAC Official Method 942.05 Ash of Animal Feed. A method recognized for starch analysis is set forth in AOAC 996.11 Starch (Total) in Cereal Products. Moisture analysis may be accomplished by any suitable method known in the art. Recognized methods for moisture analysis are set forth in AOAC Official Method 930.15 Loss on Drying (Moisture) For Feeds, and AOAC Official Method 935.29 Moisture in Malt. As should be understood, any suitable method of measuring the content of protein, fat, ash, starch and moisture which are equivalent to the AOAC methods mentioned herein may be utilized as well.

The dry weight values of SS, NSSO, protein, fat, ash and starch are used to calculate the mass balance closure and the fiber. Furthermore, as is known, moisture analysis is required to calculate dry weight values. Alternatively, the as-is values of SS, NSSO, protein, fat, ash, starch and moisture can be used to calculate the mass balance closure and the fiber content.

Soluble Saccharides Analysis

In accordance with the disclosure, the novel soluble saccharides analysis is described hereinbelow. In addition, any sub-processes referred to that are known in the art are incorporated by reference as if fully stated herein.

Soluble Saccharides Analysis

According to the disclosure, the amount of Soluble Saccharides present in any given substrate can be determined by extraction followed by the analysis by HPLC. The measured saccharides are then used to calculate the total Soluble Saccharide content of the sample. The non-saccharide soluble organics are quantified using another method according to the disclosure as described hereinbelow. If analyzing for both soluble saccharides and non-saccharide soluble organics, only one extraction and HPLC analysis needs to be performed per sample—the extract can be used to capture all analytes via HPLC-RI using an appropriate analytical column.

An example of the method for testing the amount of soluble saccharides generally includes the steps of:

1. Ensure test sample has moisture percentage of <15%, if >15% then dry test sample without exceeding test sample temperature of 50° C.
2. Grind test sample such that test sample can pass through a 0.5 mm screen. The test sample, before or after grinding, may be retained in a desiccator if not to be used immediately to ensure the test sample does not absorb moisture from ambient air.
3. A Total Solids Measurement is conducted on the dried test sample in accordance with AOAC 935.29.
4. Weigh out 5.0±0.25 g of the ground test sample into a centrifugal tube and record weight to the nearest 0.0001 grams.
5. Add 20.0 mL of Type 1 DI water to the centrifuge tube and record the weight of the added water. If using a repeater to draw water, the first 20 mL may be drawn to remove any air from the system.
6. Cap centrifuge tube.
7. Steps 4-6 may be repeated multiple times to acquire a plurality of testable samples. An average weight of the water is determined if multiple test samples are made. An additional sample may be created using a reference material to validate test results.
8. Stir centrifugal tube vigorously on vortex mixer to ensure entire test sample goes into suspension.
9. Incubate the test sample in a hot water bath. The hot water bath temperature and duration is dependent upon the starch content of the test sample. If the test sample has a starch content of >25%, the test sample is incubated for 14 to16 minutes at 50° C. to deter gelatinizing of the test sample. If the test sample has a starch content of <25%, incubation will be at 95° C. for 115 to 125 minutes, with an included mixing of the sample on the vortex mixer after 30 minutes of incubation.
10. Remove from the hot water bath and mix on the vortex mixer vigorously until the test sample is again in suspension.
11. Centrifuge for 5 minutes at 5,000 rpm to form a supernatant.
12. Test a portion of the supernatant for density via ASTM D4052 method.
13. Filter remaining portion of the supernatant, such as with a syringe fitted with syringe filter, and fill an HPLC vial with filtered supernatant.
14. Analyze sample on HPLC to achieve saccharide values for: DP4+, maltotriose, maltose, glucose, fructose/xylose/galactose, and arabinose. It should be noted that methods equivalent to use of an HPLC may be utilized.
15. Calculate the % dry weight of all saccharides using the HPLC results.

Non-Saccharide Soluble Organics Analysis

In accordance with the disclosure, the Non-Saccharide Soluble Organics Analysis is provided hereinbelow. All sub-processes mentioned that are known in the art are incorporated by reference as if fully stated herein.

Non Saccharide Soluble Organics Analysis

1. Ensure test sample has moisture percentage of <15%, if >15% then dry test sample without exceeding test sample temperature of 50° C.
2. Grind test sample such that test sample can pass through a 0.5 mm screen. The test sample, before or after grinding, may be retained in a desiccator if not to be used immediately to ensure the test sample does not absorb moisture from ambient air.
3. A Total Solids Measurement is conducted on the dried test sample in accordance with AOAC 935.29.
4. Weigh out 5.0±0.25 g of the ground test sample into a centrifugal tube and record weight to the nearest 0.0001 grams.
5. Add 20.0 mL of Type 1 DI water to the centrifuge tube and record the weight of the added water. If using a repeater to draw water, the first 20 mL may be drawn to remove any air from the system.
6. Cap centrifuge tube.
7. Steps 4-6 may be repeated multiple times to acquire a plurality of testable samples. An average weight of the water is determined if multiple test samples are made. An additional sample may be created using a reference material to validate test results.
8. Stir centrifugal tube vigorously on vortex mixer to ensure entire test sample goes into suspension.
9. Incubate the test sample in a hot water bath. The hot water bath temperature and duration is dependent upon the starch content of the test sample. If the test sample has a starch content of >25%, the test sample is incubated for 14 to16 minutes at 50° C. to deter gelatinizing of the test sample. If the test sample has a starch content of <25%, incubation will be at 95° C. for 115 to 125 minutes, with an included mixing of the sample on the vortex mixer after 30 minutes of incubation.
10. Remove from the hot water bath and mix on the vortex mixer vigorously until the test sample is again in suspension.
11. Centrifuge for 5 minutes at 5,000 rpm to form a supernatant.
12. Test a portion of the supernatant for density via ASTM D4052 method.
13. Filter remaining portion of the supernatant, such as with a syringe fitted with syringe filter, and fill an HPLC vial with filtered supernatant.
14. Analyze sample on HPLC to achieve non-saccharide soluble organic values for: lactic acid, glycerol and acetic acid. It should be noted that methods equivalent to use of an HPLC may be utilized.
15. Calculate the % dry weight of all non-saccharide organics using the HPLC results.

After the preprocessed grain material and/or post processed grain residuals are tested by the conventional proximate analysis tests, and by the novel SS and NSSO assays, the values of the test results are used to calculate a mass closure on the sample and to calculate fiber. The novel Solubles Assays in conjunction with the traditional proximates analyses of protein, fat, starch, and ash provides a novel method of accurately determining fiber by mass closure calculation. The calculation is Fiber=100-protein-fat-starch-ash-Solubles (SS and NSSO). This enables the quantification of in situ D3 RINS from a dry mill ethanol plant.

As can be seen below, the method disclosed herein provides for far greater accuracy over conventional, prior art analysis of proximates (protein, fat, starch, ash), wherein an unacceptable percentage of the mass of pre-processed grain materials and post processed grain residuals is currently unknown. The complete mass closure provided according to the disclosure enables the fiber content to be calculated in lieu of measuring fiber. Data has shown the manner of calculating fiber in accordance with the disclosure is more precise than measuring fiber by the conventional neutral detergent fiber (NDF) assay.

| Exemplary Testing Results | | | | | | | |
|---|---|---|---|---|---|---|---|
| Prior art typical results for pre-processed material | | | | | | | |
| Starch | Ash | Fat | Protein | Fiber (NDF) | Unknown | | |
| 65.4% | 2.1% | 5.1% | 9.2% | 8.1% | 11.0% | | |
| Mass closure for pre-processed material according to disclosure | | | | | | | |
| Starch | Ash | Fat | Protein | Fiber | SS | NSSO | |
| 65.4% | 2.1% | 5.1% | 9.2% | 10.9% | 5.9% | 1.4% | |
| Prior art typical results for post-processed material | | | | | | | |
| Starch | Ash | Fat | Protein | Fiber (NDF) | Unknown | | |
| 2.1% | 6.5% | 15.6% | 31.9% | 20.0% | 24.1% | | |
| Mass closure for post-processed material according to disclosure | | | | | | | |
| Starch | Ash | Fat | Protein | Fiber | SS | NSSO | |
| 2.1% | 6.5% | 15.6% | 31.9% | 29.1% | 6.6% | 8.3% | |

The table below provides the general methodology of the disclosed processes:

| Parameter | Moisture | Protein | Fat | Ash | Starch | Soluble Saccharides | Non Saccharide Soluble Organics | Fiber by Mass Closure |
|---|---|---|---|---|---|---|---|---|
| Analytical Method: | AOAC 935.29 | AOAC 990.03 | AOAC 945.16 | AOAC 942.05 | AOAC 996.11 with wash | SS | NSSO | FMASS |
| Units: | % | % dw | % dw | % dw | % dw | % dw | % dw | % dw |
| [1]Pre and Post-Process Samples | | A | B | C | $D_w$ | E | F | 100-A-B-C-$D_w$-E-F |

[1]When analyzing Pre and Post-Process Materials, the Starch method used does include a wash step; therefore, the soluble saccharides will not be included in the starch result.

The accurate determination of fiber is critical to determining the Converted Fraction for the generation of D3 RINS by the EPA's in situ renewable fuels pathway. The solubles assays on pre and post processed materials in accordance with the disclosure coupled with the calculation of fiber by mass closure allows for the accurate quantification of fiber, which enables the quantification of in situ D3 RINS from a dry mill ethanol plant. Non-limiting examples of applicability of the method of the disclosure would be in the in situ renewable fuels pathway from a dry mill ethanol plant, and any other process for converting fiber, including processes that convert fiber separate from starch and cellulosic processes. The solubles assays of the disclosure coupled with the calculation of fiber by mass closure may also be applied in the area of animal nutrition.

In another embodiment, the calculation of cellulosic content is determined without a wash step, which is in contrast to that shown in the table above. In this embodiment, the protein, fat, and ash content are determined as described above. However, the sample does not include a wash step which removes the necessity to all perform a separate soluble saccharides (SS) analysis. The starch assay uses enzymes, alpha amylase in first incubation followed by a glucoamylase in a second incubation, to convert the starch to glucose. The starch assay measures glucose and then the starch content can be calculated from the glucose measurement. Any soluble saccharides that cannot be enzymatically converted to glucose will stay with and be included as part of the cellulosic content. In the other methods described above, the soluble saccharides were washed off before the enzymatic starch assay was performed thereby also requiring a soluble saccharide content assay. However, the soluble saccharides in this embodiment are included as part of the starch content if they can be converted to glucose and if they cannot be converted to glucose they are included in cellulosic content.

Cellulosic content (fiber) by mass closure using un-washed starch:

| Parameter | Protein | Fat | Ash | Un-Washed Starch | Non Saccharide Soluble Organics | ASTM Cellulosic Content (Fiber) |
|---|---|---|---|---|---|---|
| Analytical Method: | AOAC 990.03 | AOAC 945.16 | AOAC 942.05 | AOAC 996.11 | SO.NSSO | Cellulosic Content by Mass Closure SO.FMASS |
| Units: | % dw A | % dw B | % dw C | % dw D | % dw E | % dw 100-A-B-C-D-E |

In the above graph:
 "A" is the total protein content.
 "B" is the total fat/oil content.
 "C" is the total inorganic content.
 "D" is the total starch, from an un-washed sample, and is a measurement of all starch by way of alpha and gluco-amylase conversion with no wash step utilized.

Therefore, this measurement includes all soluble mono and oligo-saccharides that can be converted to glucose using, for example, an alpha and gluco-amylase. It will not include any C5 sugars such as xylose or arabinose nor will it include any C6 sugars such as galactose or mannose that have been derived from hemicellulose because the starch assay measures the resulting glucose formed and calculates the starch content using the total glucose formed in the starch assay.

"E" is the total of all organic compounds that are not saccharides such as, for example, lactic acid, acetic acid, and glycerol.

In the total of the graph above, C5 and C6 sugars that do not enzymatically convert to glucose, i.e. calculated to Starch, will be accounted for in the cellulosic content and not count toward the measured fiber conversion. The unconverted C5 and C6 sugars will therefore be accounted for in the remaining fraction to ensure that they will be included as residual cellulosic content, i.e. fiber, and will not count toward the measured fiber conversion. In the method including the wash step, the C5 and C6 sugars would have been removed and therefore a small decrease to the cellulosic content would have occurred. Consequently, using unwashed starch will account for the C5 and C6 sugars resulting in an even higher degree of accuracy.

While the methods described above include the calculation of the total fiber, it may be of further importance to utilize the above methods to determine starch quantities both before and after cellulosic ethanol conversion. These quantities can then be used to determine a ratio of starch quantity before and after conversion. Another ratio to consider is the ratio of cellulosic content before and after conversion. These ratios can be used to determine the amount of cellulosic ethanol produced and can therefore also be used to quantify the carbon intensity of cellulosic ethanol produced for the purposes of qualification and sale under the Low Carbon Fuel Standard (LCFS) in the state of California and other, similar, LCFS programs.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the element.

I claim:

1. A method of quantifying fiber content in cellulosic feedstock by mass closure, the method comprising:
 determining moisture content of a sample of cellulosic feedstock and if the moisture content is greater than 15 wt-%, drying the sample to below 15 wt-% moisture;
 determining protein, fat, starch, and ash content of the sample on a dry weight basis;
 determining non-saccharide soluble organics content of the sample by:
  extracting lactic acid, glycerol, and acetic acid from the sample; and
  measuring amount of the lactic acid, the glycerol, and the acetic acid; and
 calculating the fiber content as 100−(% dry weight protein+% dry weight fat+% dry weight starch+% dry weight ash+% dry weight non-saccharide soluble organics).

2. The method of claim 1, wherein the measuring of the amount of the lactic acid, the glycerol, and the acetic acid is done via HPLC.

3. The method of claim 1, wherein the extracting of the lactic acid, the glycerol, and the acetic acid from the sample comprises:
 grinding a portion of the sample to provide a ground sample;
 mixing the ground sample with water to provide a suspension;
 incubating the suspension; and
 separating a supernatant from the incubated suspension.

4. The method of claim 1, wherein the cellulosic feedstock comprises processed grain residuals from an ethanol production process.

5. The method of claim 1, wherein the cellulosic feedstock comprises animal feed.

6. The method of claim 1, wherein the method comprises quantifying fiber content in a first sample comprising pre-process material from an ethanol production process and quantifying fiber content in a second sample comprising processed grain residuals from the ethanol production process.

7. The method of claim 5, wherein the method produces a conversion ratio.

8. The method of claim 7, wherein the method produces a converted fraction report comprising a mass closure calculation of pre-process grain material and processed grain residuals from an ethanol production process.

9. The method of claim 8, wherein the mass closure calculation comprises calculating a fiber content of the pre-process grain material and the processed grain residuals as 100−(% dry weight protein+% dry weight fat+% dry weight starch+% dry weight ash+% dry weight non-saccharide soluble organics).

10. The method of claim 9, wherein the % dry weight protein, the % dry weight fat, the % dry weight starch, and the % dry weight ash are determined using AOAC official methods and the % dry weight non-saccharide soluble organics is determined by extracting the lactic acid, the glycerol, and the acetic acid from the pre-process grain material and the processed grain residuals and measuring the amount of the lactic acid, the glycerol, and the acetic acid via HPLC.

11. The method of claim 1, wherein the % dry weight starch is determined without a wash step.

\* \* \* \* \*